United States Patent [19]
Davison

[11] Patent Number: 5,263,957
[45] Date of Patent: Nov. 23, 1993

[54] ULTRASONIC SCALPEL BLADE AND METHODS OF APPLICATION

[75] Inventor: Thomas W. Davison, North Attleboro, Mass.

[73] Assignee: Ultracision Inc., Smithfield, R.I.

[21] Appl. No.: 771,182

[22] Filed: Oct. 4, 1991

Related U.S. Application Data

[63] Continuation-in-part of Ser. No. 492,491, Mar. 12, 1990, Pat. No. 5,026,387, and a continuation-in-part of Ser. No. 561,092, Aug. 1, 1990, Pat. No. 5,167,725, and a continuation-in-part of Ser. No. 670,186, Mar. 15, 1991, abandoned.

[51] Int. Cl.$^5$ .............................................. A61B 17/00
[52] U.S. Cl. ................................ 606/169; 606/167; 606/171; 604/22
[58] Field of Search .............. 606/167, 169, 171, 181, 606/190, 177, 178, 176; 604/22

[56] References Cited

U.S. PATENT DOCUMENTS

| | | | |
|---|---|---|---|
| 3,636,943 | 1/1972 | Balamuth | 606/169 X |
| 3,762,243 | 10/1973 | Borrkfield | 204/129.3 |
| 3,786,814 | 1/1974 | Armao | 604/2 X |
| 4,188,952 | 2/1980 | Loschilov et al. | 606/169 X |
| 4,499,898 | 2/1985 | Knepshield et al. | 606/167 X |
| 4,885,004 | 12/1989 | Pao | 604/22 |

FOREIGN PATENT DOCUMENTS

| | | | |
|---|---|---|---|
| 0156650 | 1/1963 | U.S.S.R. | 606/167 |
| 1424814 | 10/1988 | U.S.S.R. | 606/167 |

Primary Examiner—Stephen C. Pellegrino
Assistant Examiner—Jeffrey A. Schmidt
Attorney, Agent, or Firm—Nixon & Vanderhye

[57] ABSTRACT

The ultrasonic scalpel blade includes a blade having an included blade edge angle of 25° and greater such that, upon application of ultrasonic power, the otherwise blunt blade has a perceived sharpness corresponding to the sharpness of manually used scalpel blades with the added advantage of improved coagulation and hemostasis. Blades are also provided with varying included angles for ultrasonically incising different tissues.

14 Claims, 2 Drawing Sheets

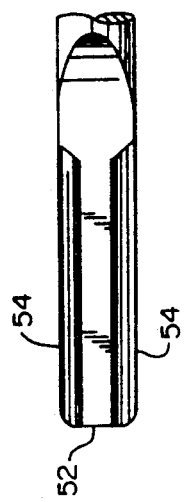
Fig. 1
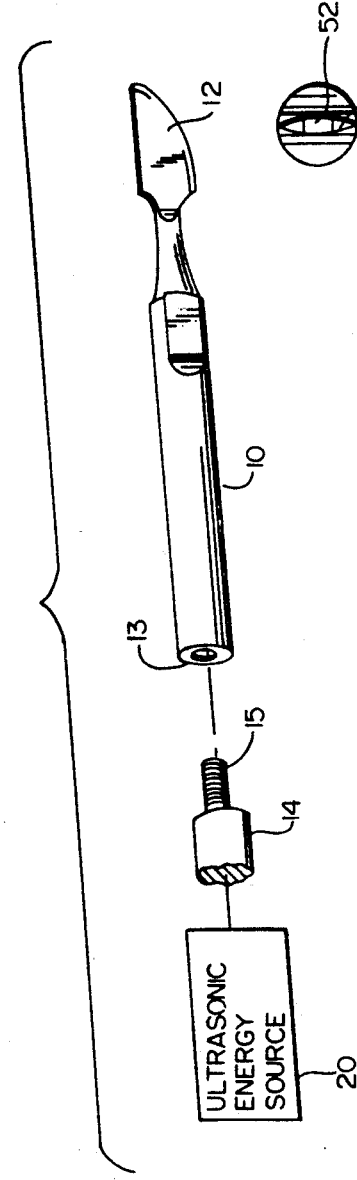
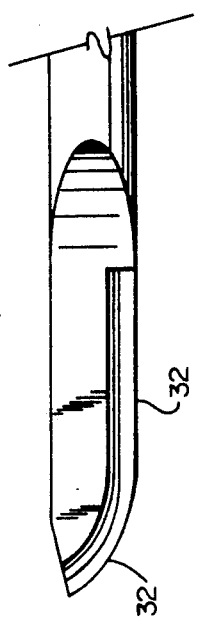
Fig. 2
Fig. 8
Fig. 9
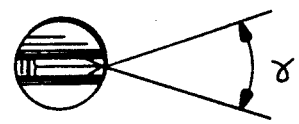
Fig. 3

ULTRASONIC SCALPEL BLADE AND METHODS OF APPLICATION

RELATED APPLICATIONS

This application is a continuation-in-part of applications Ser. Nos. 07/492,491, filed Mar. 12, 1990, now U.S. Pat. No. 5,026,387; 07/561,092, filed Aug. 1, 1990, now U.S. Pat. No. 5,167,725; and 07/670,186, filed Mar. 15, 1991, now abandoned, the disclosures of which are incorporated herein by reference.

BACKGROUND AND SUMMARY OF THE INVENTION

The present invention relates to scalpel blades and particularly to ultrasonically applied surgical scalpel blades having improved cutting and coagulation efficiency, and methods of applying the blades to a substrate for cutting.

From the advent of surgery, various types of surgical instruments for incising and dissecting human and animal tissue have been employed. It has long been a tenet of surgical procedures that the sharper the blade, the more efficient the cutting action. More modern techniques for incising and dissecting include electrosurgical cutting, which has the added benefit of affording coagulation simultaneous with the cutting. Thus, cutting with moderate or significant hemostasis can be achieved using electrosurgical techniques. Concomitantly, however, electrosurgical techniques cause significant thermal injury to tissues as a by-product of coagulation.

More recently, however, ultrasonic surgical devices for performing surgical procedures have been developed, for example, as disclosed in the above-identified applications. Generally speaking, these surgical devices are hand-held instruments connected to a source of ultrasonic energy. The ultrasonic energy is transmitted through a connection or mount between the ultrasonic energy source and a hand-held coupler which mounts the surgical tool, for example, a surgical blade mounted at the tip of the coupler. This facilitates transmission of ultrasonic energy from the ultrasonic energy source through the coupler to the surgical blade to generate ultrasonic vibrations in the blade. Until the present invention, however, the mechanism of the interaction of the vibrating blade and the adjoining tissue was not sufficiently well understood in relation to cutting and coagulation and generally it was thought that the same sharp blades used in hand-held surgical scalpels should be applied to ultrasonic surgical scalpels.

According to the present invention, it has been discovered that in ultrasonic surgical instruments of this type, coagulation is achieved while cutting by reducing the sharpness and hence increasing the dullness or bluntness of the blade in comparison with standard sharp blades. It is possible to achieve a perceived sharpness corresponding to the sharpness provided by the mechanical configuration of the sharp blade edges of standard scalpels while simultaneously achieving coagulation in the various tissues. That is to say, it has been discovered that the application of ultrasonic power to an otherwise dull blade enhances the sharpness of the blade when applied to incise and dissect and achieves simultaneous coagulation. This has been discovered by an improved understanding of the interaction of the vibrating blade and various tissues.

Heat is produced in tissue as ultrasonic blade motion couples with the tissue, the tissue moving with the blade surface. The mechanical energy within the tissue is converted to heat as a result of the friction and shear stress within the tissue which breaks chemical bonds that give the protein structure. The heat and mechanical energy cause the highly structured protein, i.e., collagen and muscle protein, to denature, i.e., become less organized, into a white coagulum. Coagulation is a function of the blade velocity, the extent of blade and tissue coupling and the duration of the contact between the blade and the tissue. Blade velocity is a function of ultrasonic frequency and amplitude or displacement per cycle. Thus, at constant frequency, displacement is a function of the electrical power input to the transducer. Coupling of the blade motion to the tissue requires adequate force between the blade and tissue, friction and surface area. The blade surfaces may not, therefore, be lubricious. To the contrary, high friction coefficients of blade material are therefore desirable.

With respect to cutting and coagulation, the magnitude of the heat produced is inversely proportional to the blade sharpness and incision or dissection speed. Sharp blades pass through the tissue with less force and less tissue coupling, hence less coagulation is produced. Thus, in order to achieve tissue coagulation and hemostasis, ultrasonic scalpel blades cannot be as sharp as surgical scalpel blades; furthermore, ultrasonic scalpel blades do not need to be as sharp as standard scalpel blades because the ultrasonic motion enhances the sharpness and the cutting is perceived to be as sharp or sharper than standard scalpel blades. The ultrasonic motion essentially compensates for the reduced sharpness of the blade. That advantage affords another benefit in that substantial heat and mechanical energy input to the tissue enables coagulation.

This discovery of the mechanism of cutting and coagulation with ultrasonic scalpel blades not only has led to the conclusion that relatively dull blades should be utilized in ultrasonic scalpel applications but also that the degree of sharpness or dullness of the blade edge affects coagulation in different tissue. For example, in skin and muscle tissue with high protein content, a relatively sharp blade may efficiently cut through the skin and muscle with minimum heat generation and mechanical coupling to the tissue because of the protein-rich environment which more readily produces the white coagulum necessary to seal a blood vessel. However, in less dense tissue, such as fat, fascia and parenchyma, where little collagen or protein is available to facilitate coagulation of bleeders during incisions, a less sharp or more dull blade is used. During ultrasonic motion of the blade through the collagen or protein-poor tissue, the blade will coapt the blood vessel before cutting through it with sufficient mechanical energy generated to form the coagulum necessary to attain hemostasis. Furthermore, effective cutting in less dense tissues can be achieved with very dull ultrasonic scalpel blades as these tissues are generally easier to cut.

The application of ultrasonic energy to scalpel blades in different tissues and conditions of surgery has required development of a variety of blades and blade edge geometries to achieve the necessary sharpness or dullness, depending upon the application.

In accordance with the present invention, it has been found that increasing the angle of the blade edge faces causes (i) the reduction in sharpness necessary to improve the coupling of ultrasonic motion with the tissues and (ii) blood vessel compression during cutting. It has been found that applying ultrasonic energy to a typically sharp scalpel blade results in virtually little or no coagulation.

It has also been found that because of the different tissues through which incisions or dissections are made, different blade edges having different included angles are desirable for ultrasonically actuated blades. These can be provided in blades having different included angles or a single blade having discrete blade edges with different included angles and hence different dullness or sharpness. With respect to the sharpness of the blade, typically a sharp scalpel of conventional design and used manually has an included blade edge face angle of 22° and, as noted previously, the trend has been toward ever-increasing sharpness of that blade with smaller included angles. In accordance with the present invention, however, an included blade edge face angle of 25°–50° has been found satisfactory, with a perceived sharpness corresponding to the sharpness of a typical blade having a blade edge of approximately 22°. Also, the various and different tissues to be incised to a large extent optimally determine the degree of dullness of the blade. For example, a blade edge face angle of about 25° with a hard sharpenable edge of NiCr alloy or beta titanium may achieve hemostasis in dermatologic, plastic and opthalmic surgery, with very slow cutting. The degree of perceived sharpness is greater or equal to an extremely sharp standard, manually applied, scalpel blade. For cutting tissue with high protein concentration, for example, skin and muscle, with average sharpness and excellent hemortasis, a blade edge face angle of between 30°–40° using a nickel chrome or beta titanium alloy coating on the edge may be employed. While a blade of this type may also cut fat, fascia, connective tissue and parenchyma with excellent sharpness, it does not readily cut highly elastic dense structures such as large blood vessels, nerves and outer linings of many structures of the alimentary canal, urogenital system and the gall bladder. A blade of this type, however, is ideal for endoscopic surgery.

For cutting skin and muscle with fair sharpness, a blade edge face angle of 40°–50° with a nickel chrome or beta titanium alloy coating may be used. This blade edge can be used to dissect through fat with good hemostasis and solid parenchymas tissue with fair hemostasis during fat and fascia plane dissection.

A blade formed entirely of aluminum or titanium without a coated edge and having a blade edge face angle of 25°–45° provides hemostatic blunt dissection in fat and through tissue planes between skin and fat and fat and fascia. Blood vessels up to three millimeters may be coagulated during these dissections.

Blade edge design may thus be optimized for procedures where only one tissue type is incised. That is, a particular blade edge face angle for a particular tissue is provided for optimizing cutting and coagulation. However, where two or more tissues are to be incised, dual-edge blades may overcome the deficiencies of a blade optimized for only one type of tissue. Hence, in accordance with the present invention, a blade having one section formed to have an included blade edge face angle, for example, on the order of about 25°–35° and another section having a different included blade edge face angle, for example, on the order of 25°–45°, may be provided. Consequently, the one blade section may be used for incision of one tissue type, while the other blade section may be used for the incision of another tissue type. A variable edge may also be provided. For example, to cut full skin thickness in the scalp and forehead with hemostasis, a variable blade edge that is sharp, i.e., about 25°–35° on a straight section and through one-half of the radius and less sharp, i.e., more dull (45° or more or formed of aluminum), through the remainder of the radius and tip is effective for full skin thickness scalp incisions. The dull tip can penetrate the skin when ultrasonically activated since the skin is supported and backed by the skull bone. The sharp blade edge on the straight section cuts the skin with ease and is hemostatic because of the high collagen concentration in the skin. The blunt tip and radius cuts and coagulates the extensive subcutaneous vascular plexus that lies beneath the skin in the thin subcutaneous fat layer. The relatively blunt edge near and at the tip compresses the vascular plexus against the skull bone and seals the vessels as they are cut.

Full thickness skin incisions using a blade edge having an included blade edge face angle of 20°–40° is very hemostatic in the skin. However, should the incision extend into fat, some bleeding is encountered. By rounding the blade tip, coagulation in the deep dermis and fat is improved. The curved tip is also ideal for endoscopic applications because it reduces the risk of accidentally puncturing internal structures.

In a preferred embodiment according to the present invention, there is provided a blade for an ultrasonic scalpel having a cutting edge defined by a pair of cutting edge faces having an included angle of at least about 25° whereby a perceptively sharper blade and coagulation of the blood vessels in the incision upon application of ultrasonic power to the blade are obtained.

In a further preferred embodiment according to the present invention, there is provided a method of incising tissue comprising the steps of selecting an ultrasonically actuated scalpel blade from a plurality of blades each having different included and increasing blade angles of at least about 25° in inverse proportion to the protein content of the tissue to be incised and applying energy to the selected blades to ultrasonically vibrate the blades thereby to achieve substantially simultaneous cutting with perceived enhanced sharpness and hemostasis.

In a still further preferred embodiment according to the present invention, there is provided a method of incising different tissues employing a single scalpel blade comprising the steps of providing an ultrasonically actuated scalpel blade having at least two discrete edge portions with different included angles, both being at least 25°, applying one of the discrete edge portions to one of the tissues to dissect the one tissue, applying energy to the blade to ultrasonically vibrate the blade to achieve cutting and hemostasis of the one tissue, applying the other edge portion to the other of the tissues and applying energy to the blade to ultrasonically vibrate the blade when the other edge portion is applied to the other tissue to achieve simultaneous cutting and hemostasis in the other tissue.

In a still further preferred embodiment according to the present invention, there is provided a method of incising tissue comprising the steps of selecting an ultrasonically activated blade from a plurality of blades each having different included and increasing blade angles thereby affording blades that are less than surgically sharp and having a bluntness and dullness in inverse proportion to the protein content of the tissues to be incised and applying energy to the selected blades to ultrasonically vibrate the blade thereby to achieve tissue coagulation and hemostasis and simultaneously achieve a cutting sharpness that is perceived to be at least equivalent to the sharpness of standard surgical blades.

Accordingly, it is a primary object of the present invention to provide a novel and improved ultrasonic actuated scalpel blade having improved cutting and coagulation characteristics.

These and further objects and advantages of the present invention will become more apparent upon reference to the following specification, appended claims and drawings

BRIEF DESCRIPTION OF THE DRAWING FIGURES

FIG. 1 is a schematic perspective view of a scalpel blade according to the present invention connected to a blade coupler and an ultrasonic energy source;

FIG. 2 is an enlarged fragmentary side elevational view of a scalpel blade according to the present invention;

FIG. 3 is an end view thereof illustrating the included angle;

FIGS. 8 and 9 are side and end elevational views, respectively, of a still further form of blade hereof.

DETAILED DESCRIPTION OF THE DRAWING FIGURES

Figure 5:
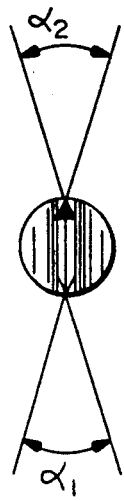
FIG. 5 is an end elevational view thereof.

Reference will now be made in detail to a present preferred embodiment of the invention, an example of which is illustrated in the accompanying drawings.

Referring now to the drawing figures, particularly to FIG. 1, there is illustrated a blade coupler 10, having a blade element or scalpel blade 12 at one end and a screw thread for coupling the opposite end of the blade coupler to an acoustical mount 14. For example, the blade coupler 10 is internally threaded at 13 at one end for receiving the external threads of a male connecting portion 15 on the acoustical mount 14. It will be appreciated that this type of connection is illustrative only and that other types of connections may be formed whereby acoustical energy may be transmitted from the acoustical mount to the blade coupler and to the blade. The acoustical mount, in turn, is coupled to a source of ultrasonic energy, designated 20, whereby ultrasonic energy is provided the blade 12. Generally, the ultrasonic energy source supplies ultrasonic energy at a constant frequency to the blade whereby the blade velocity is a function of the electrical power input to the transducer.

As indicated previously, the blade does not need to be mechanically sharp as are standard disposable scalpel blades in order to have a perceived sharpness corresponding to the sharpness of such standard blades. The ultrasonic motion enhances the sharpness. That is, hemostatic skin and muscle incisions can be made with a high degree of perceived sharpness because the ultrasonic motion compensates for the actual reduced sharpness or bluntness of the blades hereof. Thus, the ultrasonic blade is not surgically sharp but can be made surgically sharp by ultrasonically vibrating the blade, with the added benefit that the non-surgically sharp, i.e., dull or blunt blade, enables coupling of the blade to the tissue to effectively coagulate the tissue to achieve hemostasis. Also, for certain types of tissues such as the less dense tissues of fat, fascia and parenchyma, which contain little collagen or protein to facilitate coagulation, the small blood vessels thereof are readily and easily coagulated using a relatively sharp blade. However, these tissues sometimes have relatively large vessels, on the order of 1-3 millimeters in diameter, and by providing relatively dull blades, the fat, fascia and parenchyma can be excised or dissected, with the blunt edge collapsing and sealing the relatively large blood vessels as the dull blade passes through them. These tissues are more easy to cut, more dense than skin or muscle; therefore, less sharp or blunt blades cut these tissues easily when ultrasonically activated. Increasing power to the ultrasonically actuated blade increases the amplitude of the vibratory movement at constant frequency and is thus an effective method of adapting a particular dull blade to a particular type of tissue for cutting and coagulation.

In accordance with the present invention, it has been found that the ultrasonic blade edge geometry is significant in effectively cutting the tissue and coagulating the blood vessels. More particularly, it has been found that by increasing the included angle of blade edge, the reduction in sharpness can be compensated for by the ultrasonic movement, while the now relatively blunt or dull blade improves the coupling of the ultrasonic motion with the tissue and blood vessel compression during cutting to achieve coagulation and hemostasis. It has been found that an included blade edge angle of between 25°-50° and particularly a hollow ground (ground with a concave radius, for example, from a 7-inch diameter wheel) is particularly effective for use in ultrasonic scalpel blades. The blade edge angle, of course, can be less if the grind is flat and not hollow-ground. Blade material has been found to not particularly influence the cutting and coagulation and the blades may be fabricated from titanium, aluminum or stainless steel or variously coated.

It has been found that the best blade materials are aluminum or titanium. Blades comprised of these materials to not generate significant heat when ultrasonically activated. The aluminum blade dissipates heat that is generated in the tissues during coagulation. The aluminum blade is preferably coated with a nickel chrome alloy (80% nickel and 20% chromium) by a detonation spray process prior to sharpening. The titanium blade is preferably coated with a harder beta titanium alloy by welding prior to sharpening.

With respect to blade edge geometry, it has been found that the same included blade edge is not ideal for all tissues and surgical techniques. Thus, certain included angles of the blade edge are more ideal for certain types of tissues. For example, an ultrasonically actuated blade having a nickel chrome or beta titanium edge angle of 20°-25° cuts tissues with extreme sharpness, even greater than a standard scalpel blade edge. This blade edge is useful for cutting loose, unsupported skin, muscle and dense, highly elastic tissue and has application in dermatologic, plastic and opthalmic surgery. Hemostasis is achieved with this blade edge angle with very slow cutting.

A nickel chrome coated blade edge having a nickel chrome or beta titanium edge included angle of between 30°-40° has been found useful for cutting skin and muscle (with high protein concentration) with average sharpness and excellent hemostasis. Hemostasis is achieved at normal cutting rates in skin and muscle and can be achieved in fat during cutting. While this blade edge cuts fat, fascia, connective tissue and parenchyma with excellent sharpness, it will not readily cut highly elastic dense structures, such as large blood vessels, nerves in the outer linings of many structures of the alimentary canal, urogenital system and the gall bladder. This lever of selective cutting is ideal for endoscopic surgery where control of cutting is important.

A scalpel blade having a nickel chrome or beta titanium edge included angle of between 40°–50° has been found particularly useful for cutting skin and muscle which has been supported, i.e., backed by bone or a hard surface. This blade edge angle may cut skin and muscle with fair sharpness and can be used to dissect through fat with good hemostasis and solid parenchymous tissues with fair hemostasis during fat and fascia plane (low protein concentration) dissection.

A blade formed of aluminum or titanium having a blade edge included angle of 25°–45° is particularly useful for hemostatic blunt dissection in fat through tissue planes between skin and fat and fat and fascia. It will coagulate vessels up to 3 millimeters and is most suitable for selective cutting as it cuts and dissects through fat and fascia and will not cut large blood vessels and nerves.

Referring now particularly to FIGS. 2 and 3, there is illustrated a standard profile of a scalpel blade but sharpened in accordance with the present invention to have an included angle $\alpha$ of 25° or more. This standard profile has an elongated edge portion 30 and a curved tip end 32. The included angle $\alpha$ is constant along the length of both sections 30 and 32. This blade has limited application and is optimally used where only one tissue type is incised.

Figure 4:
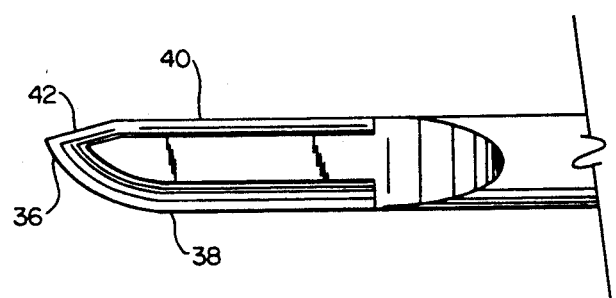
FIG. 4 is a view similar to FIG. 2 illustrating another embodiment hereof.

Referring now to FIGS. 4 and 5, there is illustrated a dual-edge blade that overcomes the deficiencies of the above-discussed standard profile blade whereby the dual-edge blade is useful for different types of tissues. For example, the curved front edge 36 and the longitudinal extending portion 38 has a nickel chrome or beta titanium coating sharpened for skin and muscle cutting, i.e., to have an included angle $\alpha_1$ of 25°–35°. The uncoated aluminum or titanium back side of the blade, indicated 40, including the angled edge portion 42 has been sharpened to an included angle $\alpha_2$ within a range of 25°–45° for hemostatic cutting in fat or tissue planes.

Figure 6:
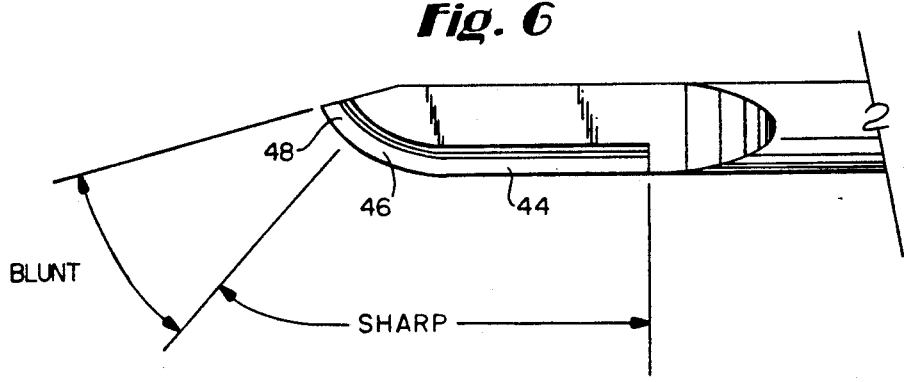
FIGS. 6 and 7 are side elevational views of still further embodiments hereof.

Referring to FIG. 6, there is illustrated a blade having a variable blade edge that is sharpened to an included angle of 25°–35° on the straight section 44 and through approximately one-half of the radius 46 and has a less sharp or more dull blade edge 48, i.e., about 45°, throughout the remainder of the radius and the tip. This blade is effective for full-skin thickness scalp incisions wherein the dull tip 48 can penetrate the skin when ultrasonically activated because the skin is supported and backed by the skull bone. The sharp blade edge of the straight section 44 cuts the skin with ease and is hemostatic because of the high collagen concentration in the dermis. The blunt tip and radius cuts and coagulates the extensive subcutaneous vascular plexus that lies beneath the skin in the thin subcutaneous fat layer. The relatively blunt edge 48 near and at the tip compresses the vascular plexus against the skull bone and seals the vessels as they are cut.

Figure 7:
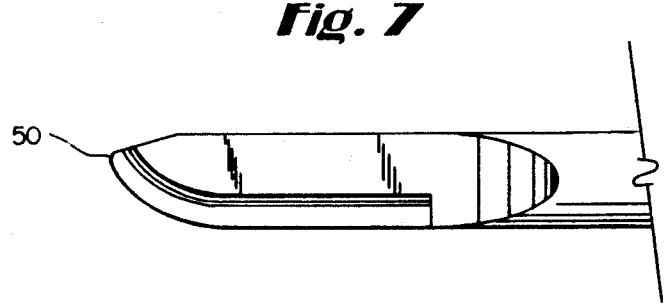

FIG. 7 illustrates a blade for full thickness skin incisions using a No. 15 blade geometry profile with a 25°–40° included blade angle whereby hemostasis is readily achieved in the skin. However, when the incision extends into the fat and some bleeding is encountered, rounding the blade tip as at 50 improves coagulation in the deep dermis and fat. It has been found that the curved tip is also ideal for endoscopic applications and reduces the risk of accidentally puncturing adjacent internal structures.

FIGS. 8 and 9 illustrate a blade that provides ultrasonic fragmentation of low density tissues at the flattened tip 52 and provides tissue cutting and simultaneous coagulation along opposite blade edges 54. The blade edge profile can be flat to maximize the tip surface area for optimal tissue fragmentation dissection. A blade with dual flat edges and flattened tip is ideal for laparoscopic cholecystectomy (endoscopic gall bladder removal). The flat tip reduces the risk of accidental puncturing adjacent structures and it aids in dissection of the gall bladder from the low density liver tissue.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A blade for an ultrasonic scalpel for use in cutting tissue comprising an elongated blade body having an elongated axis, a cutting edge extending continuously along an edge of said blade on one side of said axis and defined by a pair of cutting edge faces extending continuously and uninterruptedly along said cutting edge, said cutting edge faces having an included angle of at least about 25° affording a blunt cutting edge and substantial frictional coupling of the blade edge and tissue to obtain tissue motion with resulting generation of heat in the tissue whereby, upon application of ultrasonic power to the blade and of the blade to the tissue, a perceptively sharper blade is provided for simultaneous cutting of the tissue and coagulation of an incision are obtained, said blade having a second cutting edge extending continuously along an edge of said blade and having cutting edge faces with a different included angle as compared with the first mentioned included angle.

2. A blade according to claim 1 wherein said first cutting edge portion has a pair of cutting edge face portions defining an included angle of at lest about 25° and said second cutting edge portion has a pair of cutting edge face portions defining an included angle within a range of at least 25° to 50°.

3. A blade according to claim 1 wherein said first and second cutting edge portions lie along opposite sides of the axes of said blade.

4. A blade according to claim 3 wherein said first cutting edge portion has a beta titanium alloy edge and said second cutting edge portion is formed of titanium.

5. A blade according to claim 1 wherein said first and second cutting edge portions are formed of different materials.

6. A blade according to claim 1 wherein said first cutting edge portion has a pair of cutting edge face portions having an included angle of at least about 25° along a curved edge on one side of said blade, said second cutting edge portion having a pair of cutting edge face portions having an included angle of about at least 25° to 50° along the other side of said blade.

7. A blade for an ultrasonic scalpel comprising a blade body having first and second cutting edges each defined by a pair of cutting edge faces, each said pair of cutting edge faces having an included angle of at least about 25° whereby a perceptively sharper blade and coagulation of the blood vessels in the incision upon application of ultrasonic power to the blade is obtained;
the cutting edge faces of said first and second cutting edges, respectively, having different included angles; and
said first and second cutting edges lying along one side of said blade.

8. A blade according to claim 7 wherein said first cutting edge portion extends along a straight section of the cutting edge along one side of said blade and has cutting edge faces defining an included angle within a range of about 25°-35° and said second cutting edge portion extends along a curved section of the cutting edge along said one blade side and has cutting edge faces defining an included angle of at least about 40°.

9. A blade according to claim 8 wherein said first cutting edge portion extends along a portion of said curved section.

10. An ultrasonic scalpel for use in cutting tissue comprising a blade including an elongated blade body having an elongated axis, a cutting edge extending continuously along an edge of said blade on one side of said axis and defined by a pair of cutting edge faces extending continuously and uninterruptedly along said cutting edge, said cutting edge faces having an included angle of at least about 25° affording a blunt cutting edge and substantial frictional coupling of the blade edge and tissue to obtain tissue motion with resulting generation of heat in the tissue whereby, upon application of ultrasonic power to the blade and of the blade to the tissue, a perceptively sharper blade is provided for simultaneous cutting of the tissue and coagulation of an incision are obtained, a handle for mounting the blade, means for applying ultrasonic energy to the blade through the handle to vibrate the blade in the direction of the axis of said blade, said blade body lying in a plane, said included angle lying in a plane normal to said blade body plane and intersected by the axis of said blade body, said blade tip being flattened to provide ultrasonic tissue fragmentation upon application of ultrasonic power.

11. A method of incising tissue comprising the steps of:
selecting an ultrasonically actuated scalpel blade from a plurality of blades each having different included and increasing blade angles of at least about 25° in inverse proportion to the protein content of the tissue to be incised;
applying energy to said selected blade to ultrasonically vibrate said blade;
applying said selected blade to the tissue;
frictionally coupling said selected blade and the tissue upon application thereof to the tissue to obtain motion of the tissue sufficient to heat the tissue and cause hemostasis of the tissue, thereby to achieve substantially simultaneous cutting and hemostasis.

12. A method of incising different tissues employing a single scalpel blade comprising the steps of:
providing an ultrasonically actuated scalpel blade lying in a plane and having at least two discrete edge portions with different included angles, both being at least 25° and lying in planes generally normal to the plane of the blade;
applying one of the discrete edge portions to one of the tissues to dissect the one tissue;
applying energy to the blade to ultrasonically vibrate the blade;
frictionally coupling said one discrete edge portion and the tissue upon application of the one edge portion to the tissue to obtain motion of the tissue sufficient to heat the tissue and cause hemostasis of the tissue thereby to achieve simultaneous cutting and hemostasis of the one tissue;
applying the other edge portion to the other of the tissues;
applying energy to the blade to ultrasonically vibrate the blade when the other edge portion is applied to the other tissue; and
frictionally coupling said other edge portion and the other tissue upon application of the other edge portion to the other tissue to obtain motion of the other tissue sufficient to heat the other tissue and cause hemostasis of the other tissue thereby to achieve simultaneous cutting and hemostasis in the other tissue.

13. A method of incising tissue comprising the steps of:
selecting an ultrasonically activated blade from a plurality of blades each having different included and increasing blade angles thereby affording blades that are less than surgically sharp and having a bluntness and dullness in inverse proportion to the protein content of the tissues to be incised;
applying energy to said selected blade to ultrasonically vibrate said blade;
applying said selected blade to the tissue; and
frictionally coupling said selected blade and the tissue upon application of said selected blade to the tissue to obtain motion of the tissue sufficient to heat the tissue and cause hemostasis of the tissue, thereby to achieve tissue coagulation and hemostasis and simultaneously achieve a cutting sharpness that is perceived to be at least equivalent to the sharpness of standard surgical blades.

14. A blade for an ultrasonic scalpel comprising a blade body having first and second cutting edges each defined by a pair of cutting edge faces, each said pair of cutting edge faces having an included angle of at least about 25° whereby a perceptively sharper blade and coagulation of the blood vessels in the incision upon application of ultrasonic power to the blade are obtained;
the cutting edge faces of said first and second cutting edges, respectively, having different included angles;
said first and second cutting edges lying along opposite sides of said blade; and
said first cutting edge having a coating of a nickel chrome alloy and said second cutting edge being formed of aluminum.

* * * * *